(12) United States Patent
Lei et al.

(10) Patent No.: US 8,911,484 B2
(45) Date of Patent: Dec. 16, 2014

(54) MULTI-AXIAL EXPANDABLE PEDICLE SCREW AND AN EXPANSION METHOD THEREOF

(76) Inventors: Wei Lei, Xi'an (CN); Zixiang Wu, Xi'an (CN)

(*) Notice: Subject to any disclaimer, the term of this patent is extended or adjusted under 35 U.S.C. 154(b) by 1376 days.

(21) Appl. No.: 12/227,284

(22) PCT Filed: May 15, 2007

(86) PCT No.: PCT/CN2007/001578
§ 371 (c)(1),
(2), (4) Date: Nov. 13, 2008

(87) PCT Pub. No.: WO2007/137493
PCT Pub. Date: Dec. 6, 2007

(65) Prior Publication Data
US 2009/0105771 A1    Apr. 23, 2009

(30) Foreign Application Priority Data

May 18, 2006    (CN) .................. 2006 2 0079009 U

(51) Int. Cl.
*A61B 17/86*    (2006.01)
*A61B 17/70*    (2006.01)

(52) U.S. Cl.
CPC ......... *A61B 17/8625* (2013.01); *A61B 17/7037* (2013.01); *A61B 17/8685* (2013.01); *A61B 2017/8655* (2013.01); *A61B 17/7032* (2013.01)
USPC ............ 606/313; 606/266; 606/304; 606/314

(58) Field of Classification Search
USPC .................. 606/71, 72, 73, 304, 313, 314
See application file for complete search history.

(56) References Cited

U.S. PATENT DOCUMENTS

| | | | | |
|---|---|---|---|---|
| 4,013,071 | A | * | 3/1977 | Rosenberg .................... 606/306 |
| 4,716,893 | A | * | 1/1988 | Fischer et al. .................. 606/66 |
| 5,209,753 | A | * | 5/1993 | Biedermann et al. ......... 606/304 |
| 5,443,467 | A | | 8/1995 | Biedermann et al. |
| 5,643,321 | A | * | 7/1997 | McDevitt ...................... 606/232 |
| 5,782,833 | A | * | 7/1998 | Haider .......................... 606/266 |
| 6,042,787 | A | * | 3/2000 | Pawliszyn ...................... 422/69 |
| 6,485,494 | B1 | * | 11/2002 | Haider .......................... 606/302 |

(Continued)

FOREIGN PATENT DOCUMENTS

| | | |
|---|---|---|
| CN | 2601636 | 2/2004 |
| CN | 2647255 | 10/2004 |
| CN | 1654026 | 8/2005 |

*Primary Examiner* — Thomas J Sweet
*Assistant Examiner* — Megan Wolf
(74) *Attorney, Agent, or Firm* — Smith, Gambrell & Russell, LLP

(57) ABSTRACT

A multi-axial expandable pedicle screw includes a hollow screw having a spherical shaped end for connecting with an adapting piece in the form of a universal joint structure. The hollow screw further includes a tip shaped end, and a bore formed inside the hollow structure having a taper shaped tip. Expansion gaps are formed in the hollow screw to uniformly set up two, three, four or more anterior fins on the hollow screw extending upward along its axial direction, from its tip to the bore. The hollow screw is configured to receive an inner needle disposed in the bore. This pedicle screw is easy to operate and provides a high degree of control in screw expansion with increased stability and reliability. At the same time, this pedicle screw reduces the occurrence of screw loosening, and screw pull-out events, and also reduces failure rates of spinal surgeries.

22 Claims, 2 Drawing Sheets

(56) References Cited

U.S. PATENT DOCUMENTS

| | | | |
|---|---|---|---|
| 6,565,567 B1* | 5/2003 | Haider | 606/266 |
| 6,575,976 B2* | 6/2003 | Grafton | 606/916 |
| 6,660,004 B2* | 12/2003 | Barker et al. | 606/328 |
| 6,840,800 B2* | 1/2005 | Kidman | 439/535 |
| 6,840,943 B2* | 1/2005 | Kennefick et al. | 606/104 |
| 7,290,972 B2* | 11/2007 | Gauthier | 411/387.1 |
| 7,491,218 B2* | 2/2009 | Landry et al. | 606/246 |
| 7,510,558 B2* | 3/2009 | Tallarida et al. | 606/102 |
| 7,794,484 B2* | 9/2010 | Stone et al. | 606/329 |
| 7,976,565 B1* | 7/2011 | Meridew | 606/232 |
| 2001/0053913 A1* | 12/2001 | Freedland | 606/73 |
| 2002/0007969 A1* | 1/2002 | Head et al. | 175/61 |
| 2004/0049197 A1* | 3/2004 | Barbera Alacreu | 606/73 |
| 2005/0004644 A1* | 1/2005 | Kelsch et al. | 607/131 |
| 2006/0120822 A1* | 6/2006 | Kaye et al. | 411/30 |

* cited by examiner

MULTI-AXIAL EXPANDABLE PEDICLE SCREW AND AN EXPANSION METHOD THEREOF

FIELD OF THE INVENTION

The invention relates to a medical apparatus, particularly, to a pedicle screw used in spinal surgeries, and, more particularly, to a multi-axial expandable pedicle screw and an expansion method using the same.

BACKGROUND OF THE INVENTION

At present, in order to treat spinal diseases such as degenerative disorders, spinal trauma, spinal tumor, spinal deformity and the like, a method of transpediclular internal fixation is widely used all over the world, with satisfactory results. The multi-axial pedicle screw traditionally used, in common international circumstances, has a structure wherein the entire screw-thread is a solid structure. The fixation strength of such a screw depends on the contact area of the screw-thread and the bone, as well as the strength of the vertebrae per se. However, it is usually not possible to maintain a strong fixation strength in a slipped vertebrae reduction during fixation and to sustain such a holding force after fixation. As a result, a failure of vertebrae reduction and fixation, or unsatisfied anatomical reduction, may occur, thus, missing the goal of the surgery. Especially, a failure due to an operated screw loosening, or even pulling out, often occurs when patients suffer osteoporosis or perform improper activities after surgery.

Previously, the Chinese utility model patent number 03262479.4 disclosed an expansion method by using an expandable screw, comprising a barrel-shaped outer cannular screw, and a gauge screw. A screw thread and square, for holding, are set at the end. Four uniformity expansion parts are cut on the tip of the outer cannular screw along its axis. The contact mechanics of the pedicle screw and the vertebrae is changed by means of a mechanical expansion provided by the utility model patent. Thus, the contact mechanics of the screw and screw path is changed when adjustments are made to the gauge screw for effectively improving fixation strength. Moreover, Chinese utility model patent number 03235808.3 disclosed another kind of hollow pedicle screw having a connecting screw thread on both its inner and outer walls, and an expansion screw rotationally installed in a cavity of the vertebral arch pedicle screw. The lower part of the cavity of the vertebral arch pedicle screw is an inner cavity structure having at least three expanding gaps extending vertically downwards along its wall and having an end for holding. The purpose of the utility model patent is to increase fixation strength (anti-pulling out) of the pedicle screw. Disadvantages of both patents are that the gauge screw (expansion screw) is uneasy to insert in a manner that allows for adjustments during an operation. Also, operating steps for a surgeon to insert and fix the end part of a pedicle screw with other components is mono-directional, which contradicts the multi-directional and multi-angular demands of an inner spinal fixing operation. Furthermore, a degree of adjustment needed in a gauge screw operated by surgeons differs in fulfilling different expandable methods, and differences of expandable degree also occur between screws, which influences the treatment effectiveness and uniformity of a pedicle screw product.

SUMMARY OF THE INVENTION

In order to overcome the above-mentioned disadvantages of the available technology, the present invention aims to provide a multi-axial expandable pedicle screw, and an expansion method using the same, which will reduce the rate of screw loosening. Also, the present invention can increase stability and reliability at the same time. In addition, the present invention, being adapted for multi-axial and multi-angle connection with other components, is also easy to operate, and provides greater control over the degree of expansion. Furthermore, the present invention not only simplifies surgery procedure steps, but can also ensure a repeatable degree of expansion with the same screw specification by adopting a rod-press design.

In order to achieve the above objectives, the technical solution of the present invention is as follows: the multi-axial expandable pedicle screw, includes a hollow screw, with a tip at an end, having a bore or blind hole formed inside the hollow structure in its entirety. The bore is taper shaped at its tip, allowing an inner needle to be disposed therein. Expansion gaps are uniformly set upon the screw extending from its tip, along its axial direction, upward to the bore. The inner needle, inserted in the bore, has a length greater than the bore's length. Another end of the screw is a spherically shaped end for connecting with an adapting piece, which adapting piece is a universal joint structure having a cavity with an open pore. An inner wall of the adapting piece at the open pore connects with a lock bolt for sealing through screw threads on the inner wall and an end coupler, and a fixation rod mounts in the cavity above the inner needle to press the inner needle.

Wherein, the spherical shaped end is actively positioned under the adapting piece, at its open pore, through an annular pad and an erection cap. The annular pad can be either an opening structure or an enclosed structure. An aperture is designed in the centre of the erection cap. The inner needle and the bore with which it fits are provided with a taper shape at their tips respectively, in which an angle of the taper of the inner needle is equivalent to, or less than, an angle of the taper of the bore at its tip, and the outer diameter of the inner needle matches the inside diameter of the bore. The length of the inner needle is more than a length of the bore, and its exposed part outside of an opening of the bore is 0.5~3.0 mm, and preferably 0.8~1.5 mm. The expansion gaps are of 60%-70% of the total length of the screw, and are structured by splitting grooves that form two or more anterior fins, and start from the tip of the screw and extend along its axial direction upward to the bore. The anterior fins are curve shaped. The adapting piece for connecting with the screw forms a U-shape in its entirety; and on the spherical shaped end of the screw there is a polyhedron shaped cavity.

Furthermore, an example features an additional annular pad, being either an opening structure or an enclosed structure, which additional pad, relative to the noted example, is needed to be placed in between the inner needle and the fixation rod.

The expansion method of the multi-axial expandable pedicle screw, adopting the multi-axial, multi-angle connecting method with other medical parts, is fulfilled by a press operation to the inner needle positioned in the bore of the screw through a rod-press technique to controllably complete an expansion process of the screw, enabling the screw to expand to 2~3 mm based on an original diameter.

The invention has significant features such as the following:

1. The present invention, employing the rod-press technique to change a contact mode of the screw and vertebrae through a mechanical expansion principle, can effectively improve the fixation strength of the pedicle screw, while obtaining user-friendly features, a simple process character, and also ensuring homogeneity in the degree of screw expansion.

2. The present invention, adopting the adapting piece with a universal joint, is able to provide an adjustment function for fixing the screw with a multi-axial and multi-angle function of fixation, which makes the screw more convenient and effective in connecting with other spinal internal fixation devices, so that it can be used for a variety of spinal orthopedic and internal fixation surgeries due to doctor-friendly operating features.

3. The present invention is adapted to realize a 2~3 mm expansion on a basis of the original diameter of the screw in a way of controllable expansion by defining the length of the inner needle, the length of the bore, and an angle correlation of two ends of the inner needle and the bore. Accordingly, the expansion degree (expansion is not the bigger the better) is controlled. The controllable expansion method plays an extremely important role in treating spine surgeries.

4. The present invention sets the appropriate length of expansion space or gaps, which only expand in the vertebrae body, and not a full-length of the screw for avoiding a risk of a pedicle burst as a result from a full-length expansion. Therefore, the present invention provides a new technical line of controlled expansion technology.

BRIEF DESCRIPTION OF THE DRAWINGS

FIG. 3-1 is an implementation of an expansion process of this invention (the inner needle is not inserted).

FIG. 3-2 is the implementation of the expansion process of this invention (the inner needle is inserted).

FIG. 3-3 is the implementation of the expansion process of this invention (the inner needle downward after squeezing).

DETAILED DESCRIPTION OF THE PREFERRED EMBODIMENT

The present invention will now be described in detail in connection with specific embodiments with reference to the accompanying drawings.

Example 1

Figure 1:
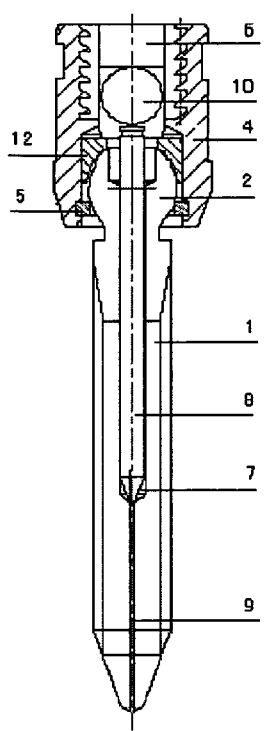
FIG. 1 is a structure of this invention.
Figure 2:
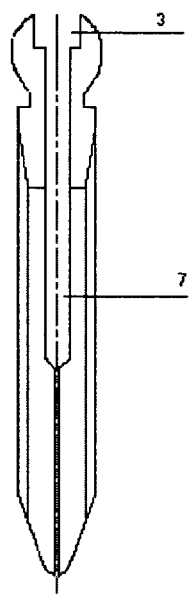
FIG. 2 is a structure of the screws of this invention.

Referring to FIGS. 1 and 2, the expansion method of a multi-axial expandable pedicle screw, adopting a multi-axial, multi-angle connecting method with other medical parts, is fulfilled by a press operation to the inner needle positioned in the bore of the screw through a rod-press technique to controllably complete an expansion process of the screw, enabling the screw to expand to 2~3 mm based on an original diameter.

Wherein, the length of the inner needle positioned in the bore of the screw is larger than the length of the bore. The part of the inner needle exposed outside of the opening of the bore is 0.8~1.5 mm (here is 0.8 mm). The expansion gaps are of 60%-70% of the total length of the screw (60% is in this example), and are structured by splitting grooves, starting from the tip of the screw and extending along its axial direction upward to the bore. The tips of anterior fins are curve shaped for avoiding a risk of pedicle fracture. The inner needle is inserted in the bore so that an inconvenient operation by adjustment can be avoided. The inner needle and the bore with which it matches are taper shaped at their tip ends respectively, with the angle of the taper of the inner needle at its tip being equal to, or less than, the angle of the taper of the bore at its tip end (it is equal in this example). The outer diameter of the inner needle matches the inside diameter of the bore for easy fulfillment of a press-in operation, after inserting the inner needle, so as to realize an expansion process of the screw, which enables the screw to expand to 2~3 mm in comparison with a previous size to complete a controllable expansion.

The multi-axial expandable pedicle screw, operable by the afore-mentioned expansion method, comprises the hollow screw 1 having the spherical shaped end 2 on one end and the tip shaped end on another end, in which the spherical shaped end 2 actively connects with the adapting piece 4. The bore or blind hole 7 has a taper shape at its tip is in a centre of the screw, with expansion gaps 9, structured by splitting with one groove to form two anterior fins, starting from the tip of the screw 1 and extending along its axial direction upward to the bore 7 (not to full length, for example, expansion gaps are 21 mm for a screw of 35 mm length). Anterior fins are of a curved shape. The spherical shaped end 2 is for actively positioning under the adapting piece 12, at its open pore, through the annular pad 5 and the erection cap 12 (the annular pad 5 can be either an opening structure or an enclosed structure positioned under the spherical shaped end 2, and the erection cap 12 being above the spherical shaped end 2). When screwing the sealing lock bolt 6 down from a top end of the adapting piece 4, through the screw thread, a fixation rod 10 is gradually pressed down in order to push the inner needle 8 into the tip end of the bore 7, for completing an expansion process, while, the spherical shaped end 2 is stably fixed in the universal-joint-structured adapting piece 4, without breaking away therefrom.

The adapting piece 4, being structured as the universal joint, forms a U-shape in its entirety. The adapting piece connects the spherical shaped end 2 of the screw 1 at a lower position, thereby functioning as a multi-axial and multi-angle screw adjustment piece. The inner wall of the U-shape, at its upper open pore, connects with the sealing lock bolt 6 through the screw thread and the end coupler. A fixation rod 10 is mounted in the cavity of the screw, above the inner needle 8 inserted in the bore, for pressing the inner needle 8.

The inner needle 8 forms a taper shape at its tip. The outside diameter of the inner needle matches the inside diameter of the bore 7 (both are the same size in this example). Both match with each other by a gap or a clearance in between. There is no inner screw thread in the bore 7, or outer screw thread on the outside of the inner needle 8 which is inserted in the bore. The length of the inner needle 8 is greater than the length of the bore 7, particularly, the inner needle extends beyond the open pore on the bore, as for instance, with 0.8 mm being exposed outside of the opening of the bore after inserting into the bore.

Figure 3:
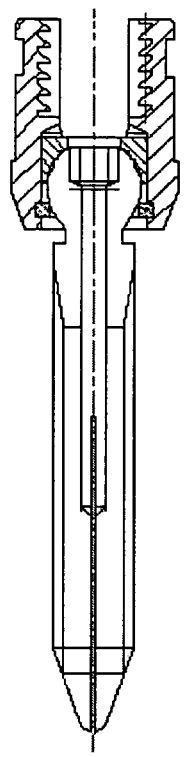
Figure 1:
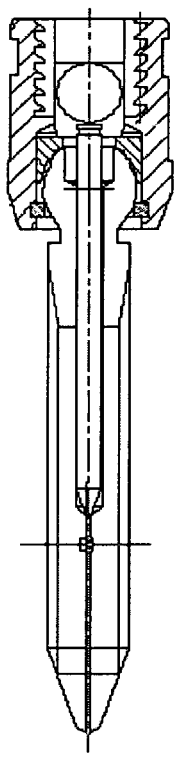
Figure 2:
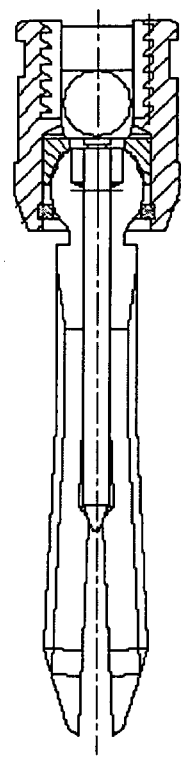

Referring to FIGS. 3-1 to 3-3, to make of use of the present invention, the hollow screw 1 is planted by holding a tool to the pedicle by the polyhedron shaped cavity 3 (six polyhedron sides in this example), and then inserting the inner needle 8 into the bore 7 of the screw 1; placing the fixation rod 10 in the adapting piece 4; directly pressing the inner needle 8 by adjusting the lock bolt 6; gradually pressing the fixation rod 10 during adjustment of the lock bolt 6 to make the tip part of the expansion inner needle 8 press against and into the tip of the bore 7, thereby resulting in the expansion gaps 9 at the tip end of the screw 1 to be opened gradually, forming a taper shape; with the expansion gaps providing a 2 mm expansion based on the original diameter in this example. This ensures meeting medical requirements and the purpose of enhancing anti-pulling out force. The expansion gaps can be restored by adjusting out the lock bolt 6 and taking the inner needle 8 out. The screw 1 can be adjusted out if it is not positioned properly.

Example 2

Figure 4:
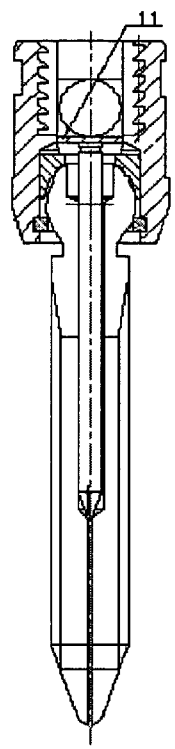
FIG. 4 is a structure of the invention of another example.

Referring to FIG. 4, this example is similar to Example 1 with the exception of: adding an annular pad 11 (it can be either an opening structure or an enclosed structure) between the inner needle 8 and the fixation rod 10 for preventing contacting surfaces of the inner needle 8 and the fixation rod 10 from damage. In this example, the screw is 45 mm in length, with four fins being formed of the expansion gaps 9, which extend along 31 mm of the screw, which is of 70% of the screw in total. After insertion into the bore, the inner needle 8 can be exposed outside of the upper opening of the bore by 1.5 mm. An expansion of 3.0 mm, in comparison with the original diameter of the screw, is realized in this example.

To use the present invention, the hollow screw 1 is planted by holding a tool to the pedicle by the polyhedron shaped cavity 3 (four regular polyhedron sides in this example), and then inserting the inner needle 8 into the bore 7 of the screw 1; placing the fixation rod 10 in the adapting piece 4 above the annular pad 5; directly pressing the inner needle 8 by adjusting the lock bolt 6; gradually pressing the fixation rod 10 during adjustment of the lock bolt 6 to make the tip part of the expansion inner needle 8 press against and into the tip of the bore 7, through the annular pad 5, resulting in the expansion gaps 9 at the tip end of the screw 1 opening gradually and the fins at tip of the screw forming a taper shape as well. A 2 mm expansion was achieved, based on the original diameter, in this example. This ensures meeting the medical requirements and the purpose of enhancing fixation strength.

Example 3

This example is similar to Example 1, with the exception of: the inner needle 8 and the bore with which it matches are provided with a taper shape at their tip ends respectively, in which the angle of the taper of the inner needle is less than the angle of the taper of the bore; and the outer diameter of the inner needle matches the inside diameter of the bore for an inserting connection. In this example, the screw is 40 mm in length, with three fins being formed of the expansion gaps 9, which extend along 26 mm of the screw, which is of 65% of the screw in total. After insertion into the bore, the inner needle is exposed outside of the upper opening of the bore by 3.0 mm. A 2.5 mm expansion was achieved in this example, in comparison with the original maximum diameter of the screw, ensuring to meet surgerical requirements.

Example 4

This example is similar to Example 1, with the exception of: the inner needle 8 and the bore with which it matches are provided with a taper shape at their tip ends respectively in which the angle of the taper of the inner needle is less than the angle of the taper of the bore. In this example, the screw is 40 mm in length, with four fins being formed of the expansion gaps 9, which extend along 28 mm of the screw, which is of 70% of the screw in total. After insertion into the bore, the inner needle 8 is exposed outside of the upper opening of the bore by 0.5 mm. An expansion of 2.2 mm was achieved in this example, in comparison with the original maximum diameter of the screw, ensuring to meet surgerical requirements.

Example 5

This example is similar to Example 1, with the exception of: the inner needle 8 and the bore with which it matches are provided with a taper shape at their tip ends respectively in which the angle of the taper of the inner needle is less than the angle of the taper of the bore. In this example, the screw is 40 mm in length, with two fins being formed of the expansion gaps 9, which extend along 24 mm of the screw, which is of 60% of the screw in total. After insertion into the bore, the inner needle 8 is exposed outside of the upper opening of the bore by 1.1 mm. An expansion of 2.2 mm was achieved in this example, on basis of the original maximum diameter of the screw, ensuring to meet surgerical requirements.

What is claimed:

1. A multi-axial expandable pedicle screw device, comprising:
    a hollow screw having a tip at an end and a spherical shaped end at another end, with a bore formed inside, the bore including an opening at the spherical shaped end of the hollow screw and a tapered tip at an intermediate location between the spherical shaped end and the tip of the hollow screw, the bore receiving an inner needle disposed therein;
    expansion gaps uniformly arranged on, and extending axially along the hollow screw, from the tip of the bore to the tip of the hollow screw;
    an adapting piece connected to the spherical shaped end of the hollow screw, the adapting piece being a universal joint having a cavity with an open pore; and
    a fixation rod mounted in the cavity above the inner needle in a manner to enable transmittance of a pressing force to the inner needle, wherein
    the inner needle disposed in the bore has a length that is greater than the length of the bore,
    the adapting piece, at the open pore, is adapted to receive a sealing lock bolt by way of a screw thread on an inner wall of the adapting piece and a coupler on the sealing lock bolt, and
    the screw device is configured such that the transmittance of a pressing force to the inner needle, from the fixation rod, will drive the inner needle into the bore to cause an expansion of the hollow screw.

2. The multi-axial expandable pedicle screw device of claim 1, wherein the spherical shaped end is positioned in the adapting piece, at its open pore, between an annular pad and an erection cap.

3. The multi-axial expandable pedicle screw device of claim 2, wherein
    the annular pad is either an opening structure or an enclosed structure; and
    the erection cap has an aperture at its centre.

4. The multi-axial expandable pedicle screw device of claim 1, wherein
    the inner needle and the bore are both provided with a tapered shape at their respective tips, and an angle of the taper of the inner needle at its tip is equivalent to, or less than, an angle of the taper of the bore at its tip; and
    the outer diameter of the inner needle matches the inside diameter of the bore.

5. The multi-axial expandable pedicle screw device of claim 1, wherein a difference in length between the inner needle and the bore is such that, when the inner needle is disposed in the bore, an exposed part of the inner needle extending outside an opening of the bore is 0.5~3.0 mm.

6. The multi-axial expandable pedicle screw device of claim 1, wherein a difference in length between the inner needle and the bore is such that, when the inner needle is disposed in the bore, an exposed part of the inner needle extending outside an opening of the bore is 0.8~1.5 mm.

7. The multi-axial expandable pedicle screw device of claim 1, wherein the expansion gaps extend along 60%-70% of the total length of the hollow screw, and are arranged to split the tip of the hollow screw to form anterior fins.

8. The multi-axial expandable pedicle screw device of claim 1, wherein the expansion gaps form two or more anterior fins which are curve shaped.

9. The multi-axial expandable pedicle screw device of claim 1, wherein the adapting piece forms a U-shape.

10. The multi-axial expandable pedicle screw device of claim 1, wherein a polyhedron shaped cavity is formed in the spherical shaped end of the hollow screw.

11. The multi-axial expandable pedicle screw device of claim 1, further comprising an additional annular pad, which is either an opening structure or an enclosed structure, and which is positioned between the inner needle and the fixation rod.

12. An method of expanding a multi-axial expandable pedicle screw device, comprising:
  connecting a pedicle screw with other medical parts;
  transmitting a pressing force to an inner needle positioned in a bore of a hollow screw, the hollow screw having a tip at an end and an adapter-mating end at another end, the bore including an opening at the adapter-mating end of the hollow screw and a tapered tip at an intermediate location between the adapter-mating end and the tip of the hollow screw, wherein
  an adapting piece is connected to the adapter-mating end of the hollow screw, and a fixation rod is received in a cavity of the adapting piece and positioned above the inner needle in the bore,
  the step of transmitting a pressing force to the inner needle includes transmitting a pressing force from the fixation rod, through a fixation-rod-press technique, to drive the inner needle into the bore of the hollow screw and thereby controllably expand the hollow screw.

13. The method of expanding a multi-axial expandable pedicle screw device according to claim 12, wherein
  the length of the inner needle positioned in the bore of the hollow screw is more than the length of the bore; and
  when the inner needle is disposed in the bore, a length of the inner needle that is exposed outside of an opening of the bore is 0.5~3.0 mm.

14. The method of expanding a multi-axial expandable pedicle screw device according to claim 13, wherein the length of the inner needle positioned in the bore of the screw is such that, when the inner needle is disposed in the bore, a length of the inner needle that is exposed outside of an opening of the bore is 0.8~1.5 mm.

15. The method of expanding a multi-axial expandable pedicle screw device according to claim 12, wherein
  the hollow screw comprises expansion gaps that extend along 60%-70% of the total length of the hollow screw, the expansion gaps being arranged to split a tip of the hollow screw to form anterior fins, and to start from the tip of the bore and extend along its axial direction to the tip of the hollow screw; and
  the method of expanding the multi-axial expandable pedicle screw device comprises expanding the hollow screw along a region corresponding to the expansion gaps.

16. The method of expanding a multi-axial expandable pedicle screw device according to claim 15, wherein the anterior fins are curve shaped anterior fins.

17. The method of expanding a multi-axial expandable pedicle screw device according to claim 12, further comprising inserting the inner needle in the bore.

18. The method of expanding a multi-axial expandable pedicle screw device according to claim 17, wherein
  the step of inserting the inner needle into the bore of the hollow screw includes inserting an inner needle having a tapered tip at its end; and
  an angle of the taper of the inner needle tip is equivalent to, or less than, an angle of the taper of the bore at its tip, and the diameter of the inner needle matches the diameter of the bore.

19. The method of expanding a multi-axial expandable pedicle screw device according to claim 12, further comprising expanding the hollow screw to between 2~3 mm.

20. A multi-axial expandable pedicle screw device, comprising:
  a hollow screw having a tip at an end and an adapter-mating end at another end, with a bore formed inside, the bore including an opening at the adapter-mating end of the hollow screw and a tapered tip at an intermediate location between the adapter-mating end and the tip of the hollow screw, the bore being adapted to receive an inner needle therein;
  expansion gaps uniformly arranged on, and extending axially along the hollow screw, from the tip of the bore to the tip of the hollow screw;
  the adapter-mating end of the hollow screw being connected with an adapting piece, in the form of a universal joint having a cavity with an open pore, the adapter-mating end being adapted such that, when an inner needle is received in the bore and the adapter-mating end is connected with an adapting piece having a fixation rod mounted in the cavity, the mounted fixation rod will be positioned above the received inner needle in a manner to enable transmittance of a pressing force to the received inner needle, wherein
  the hollow screw is adapted to receive an inner needle that has a length which is greater than the length of the bore,
  the bore is adapted to receive an inner needle in a non-threaded reception, and
  the screw device is configured such that, when an inner needle is received in the bore and an adapting piece is connected to the hollow screw, with a fixation rod received in a cavity of the adapting piece, transmitting a pressing force to the received inner needle, from the fixation rod, will drive the inner needle into the bore to cause an expansion of the hollow screw.

21. The multi-axial expandable pedicle screw device of claim 20, further comprising an inner needle received in the bore.

22. The multi-axial expandable pedicle screw device of claim 20, further comprising a fixation rod mounted in the cavity of the adapting piece.

* * * * *